United States Patent [19]
Murphy et al.

[11] Patent Number: 5,128,104
[45] Date of Patent: Jul. 7, 1992

[54] CUVETTE FOR AUTOMATED TESTING MACHINE

[76] Inventors: Harold R. Murphy, 209 N. Bellinger St., Herkimer; Jeffrey A. DuBois, R.D. #1 Box 424 Wynn Rd.; Reid A. Strickland, R.D. #1 Box 424 AA Wynn Rd., both of Holland Patent, all of N.Y. 13350; Harold F. Wood, 4 Deerpath Ct., New Hartford, N.Y. 13413

[21] Appl. No.: 539,071

[22] Filed: Jun. 14, 1990

Related U.S. Application Data

[63] Continuation-in-part of Ser. No. 425,346, Oct. 13, 1989, abandoned, which is a continuation of Ser. No. 253,383, Oct. 3, 1988, abandoned, which is a continuation of Ser. No. 42,795, Apr. 27, 1987, abandoned.

[51] Int. Cl.$^5$ .............................. G01N 21/05
[52] U.S. Cl. .................... 422/102; 206/221; 215/DIG. 8; 422/61
[58] Field of Search .............. 422/61, 102; 206/221; 215/DIG. 8; 365/246

[56] References Cited
U.S. PATENT DOCUMENTS

| | | | |
|---|---|---|---|
| 2,642,870 | 6/1953 | Smith | 215/DIG. 8 |
| 3,454,177 | 7/1969 | Bloom | 215/DIG. 8 |
| 3,582,283 | 6/1971 | Mirasol | 422/61 |
| 4,076,592 | 2/1978 | Bradley | 435/33 |
| 4,654,127 | 3/1987 | Baker et al. | 422/82.02 |

*Primary Examiner*—Robert J. Warden
*Assistant Examiner*—Timothy M. McMahon
*Attorney, Agent, or Firm*—Malin, Haley, McHale, DiMaggio & Crosby

[57] ABSTRACT

A consumable, non-reuseable cuvette for containing a sample or specimen during an automated test thereof, primarily for medical diagnostic purposes. The cuvette has a single, main reaction chamber that is pre-loaded at the factory with the precise quantity of a particular liquid or dry reagent useful for a specific test. The cover of the cuvette includes an opening to permit the introduction of a diluent or liquid reagent into the reagent chamber, a manually loaded, recessed sample receiving chamber having a frangible bottom floor and a purge reservoir. A cap is hinged to the cuvette cover and includes a rigid protruding member that pierces the sample or specimen chamber floor when closed by the testing machine, sealing the contents of the cuvette, allowing the sample to be dispensed into the chamber containing the reagent and diluent. The side walls and floor of the reaction chamber include optically transparent windows for radiant energy testing of the reagent before and after the sample is added to the reagent. Because the cap seals the contents of the cuvette, the cuvette is safely disposable after the test is completed.

8 Claims, 6 Drawing Sheets

CUVETTE FOR AUTOMATED TESTING MACHINE

This application is a continuation-in-part application of U.S. Pat. application Ser. No. 07/425,346, filed Oct. 13, 1989, now abandoned which is a continuation application of U.S. Pat. No. 07/253,383, not abandoned filed Oct. 3, 1988, and which is a continuation U.S. Pat. application No. 07/042,795, now abandoned filed Apr. 27, 1987.

BACKGROUND OF THE INVENTION

1. Field of the Invention

This invention relates to a disposable cuvette for holding a test sample or specimen, reagent, and diluent while performing a test in an automated machine, primarily for medical diagnostic purposes. The disposable cuvette can be prepackaged with a dry reagent to which a diluent is added during a test or with a liquid reagent thereby eliminating the need for the addition of a diluent in an automated test machine.

2. Description of the Prior Art

Cuvettes utilized for manual or automated medical testing are well known. In general, a procedure is established to measure the emergent wavelength of radiant energy absorbed by a sample under analysis. In a manual test, typically a technician loads a cuvette with a sample, reagent and diluent necessary to accomplish the test, each ingredient being precisely measured. The contents are mixed and the emergent radiation is observed optically or ocularly. Because the kind and precise quantity of reagent and diluent employed are critical to a successful test result, technician time and expertise to prepare and use cuvettes are significant factors to be considered with regard to cost, human error, and emergency diagnosis. Preparation time has also become a significant factor with the introduction of automated medical diagnostic machines. Such machines and their corresponding cuvettes have attempted to reduce preparation time by prepackaging various reagents and/or diluents in a container that itself ultimately houses a test performed therein. U.S. U.S. Pat. No. 3,504,376 issued Mar. 30, 1970 to Bednar et al. shows such a system.

A significant factor in the use of automated test equipment is that the reagent and the diluent must be mixed prior to the addition of the sample so that the emergent radiation from the reagent diluent mixture can provide a baseline measurement that is compared to the emergent radiation from the mixture that includes the sample. This factor precludes mixing the sample at the same time the diluent is added to the reagent. In the present invention, the sample or specimen is manually loaded in a separate chamber in the cuvette where it remains until after the reagent and diluent have been mixed and the baseline measurement of the reagent-diluent taken. The use of automated diagnostic test equipment still requires that all ingredients necessary for a specific test be precisely measured regardless of whether the cuvette is preloaded at the factory or loaded at the test site.

The use of multiple, separated compartments in testing vessels with automated machines is shown in U.S. Pat. No. 3,504,376 issued to Bednar et al on Mar. 31, 1970 (cited above); U.S. Pat. No. 4,458,020 issued to Bohn et al. on Jul. 3, 1984; and U.S. Pat. No. 4,473,530 issued to Villa-Real on Sep. 25, 1984. Each vessel shown is a complex in physical structure and requires complex interaction with the test equipment for operation.

Disposal of test containers having the residual samples and reagents therein poses a significant environmental waste problem. Washing and reusing a cuvette is not a good practice because the test results could be affected by a poorly washed cuvette. With the present invention, the cuvette remains sealed after the test and is not reusable.

As the use of prepackaged cuvettes increases in volume, reducing the cost of the manufacture and factory loading of the cuvette also becomes important.

SUMMARY OF THE INVENTION

A disposable cuvette for performing a predetermined medical diagnostic test of a specimen or sample in an automated machine comprising a hollow body shaped to form a container (having an open top) for use as a single reagent chamber. A cover is sealably attached over the open top of said body, said cover having both an aperture for introducing a diluent into the container body and a specimen receiving chamber with a frangible floor. Attached to the cover is a hinged cap that includes a post, sized and positioned to pierce the floor of the specimen chamber whenever the cap is closed over the cover. A precisely measured quantity of a reagent is loaded into the container at the factory.

The specimen receiving chamber is integrally formed within the cover and includes a frangible bottom floor that can be broken open by action of the cap post. The top of the specimen chamber may be covered by a thin hot-stamped film having a central annular opening for receiving the end of a pipette for introduction of the specimen into the specimen chamber.

The diluent dispensing aperture in the cover may include depressible flaps closely adjacent to each other but separated by an "X" shaped space. The flaps act as a closure for the body reaction chamber, but are easily opened by a diluent dispensing device.

The cover is joined and sonic welded or otherwise bonded about the upper rim of the container body itself.

The cuvette is used for testing a sample or specimen as follows. Initially when the cuvette is manufactured and prepared for market, a reagent of predetermined kind and precisely measured quantity for a particular test is placed in the container body. The cover is welded to the container body, but the cap, hinged to the cover, is not closed. A bar coded label identifying the particular diagnostic test to be performed in the cuvette is affixed to the outside wall of the cuvette body. The cuvette is then shipped with the cap in the open position to the site where the test is to be performed. A removable adhesive-backed film may be used to cover the top surface of the cover to prevent contamination prior to use.

Once at the test site, after the adhesive-backed film is removed from the cover surface, the cuvette is readied for the automated test by the introduction of the specimen into the specimen receiving chamber in the cuvette cover. This loading is done manually by a technician inserting the end tip of a pipette containing the specimen into the annular opening in the top of the specimen receiving chamber in the cuvette cover.

The cuvette (now loaded with reagent and sample in a separate chamber) is placed into a circular cuvette holder (carousel) within the automated test machine. The cuvette while in place in the carousel is moved through a series of operations in the machine as follows:

1. The carousel moves the cuvette to the bar code reading station. This identifies the test to be performed.

2. Diluent addition is performed at the second station. An automated dispensing arm pivots into position into the diluent receiving aperture of the cuvette. As diluent fills the reaction chamber, air is vented through the 0.005 inch diameter holes until diluent reaches the holes and the resulting surface tensions stops the fluid flow.

3. A vibrating action is now started to thoroughly mix the diluent and dry reagent to produce a working unit dose reagent.

4. The machine then measures the emergent radiation from the working reagent to obtain a baseline measurement, i.e. reagent absorptivity only.

5. The machine then moves the cuvette cap to a closed position over the cuvette cover forcing the post to break through the specimen chamber floor causing the patient sample (urine, serum, plasma) to flow into the chamber containing the reagent and diluent. The cuvette at this point is entirely sealed by the cap.

6. A vibrating action is now started to mix the specimen and reagent.

7. There is an incubation followed by a short vibration, then the radiant energy absorption test is performed. The difference in absorptivity of the test minus the baseline reading permits calculation of a result based upon a standard value for that test lot which is supplied by the bar code label to the instrument.

8. The cuvette can now be removed from the machine and safely discarded because the reacted specimen cannot escape from the cuvette once the cap is closed. This feature reduces or limits the release of chemicals and reacted patient samples in the hands of medical office personnel. The cuvette is not reusable.

In an alternate embodiment the invention may be used wherein a liquid reagent is introduced into the cuvette at the factory. With this embodiment and the replacement of the dry reagent, the addition of a liquid diluent during the machine test is eliminated. In order to prevent leakage of the liquid reagent an additional gasket/plug is provided on the top cover. This is essentially a planar sheet of a liquid impervious material and includes on one side a plug sized to fit firmly into the aperture in the cover that was previously used for the diluent addition. Also the cover has been modified to eliminate the vents that were required when adding liquid diluent which is used with the dry reagent.

It is an object of this invention to provide an improved cuvette that reduces the time required to prepare a cuvette for a specimen or sample test in an automated machine.

It is another object of the invention to provide a cuvette that reduces the potential for human error by including a premeasured reagent and a reagent-diluent chamber of a predetermined volume when filled for a particular diagnostic, medical test that requires a precise reagent/specimen/diluent quantity ratio.

And yet another object of this invention is to provide a disposable, non-reusable cuvette that can be used to safely dispose of the specimen and the reagent after the test is completed.

Another object of the invention is to provide a cuvette that is non-complex in manufacture, that is readily pre-loaded with a reagent at the factory, that is easily manipulated by a technician during loading of the diluent and sample, and that is suitable for use in automated diagnostic testing machines.

But yet still another object of this invention is to provide a disposable cuvette that can be used with a preloaded liquid reagent at the factory, that does not require the addition of a diluent during the test in an automatic diagnostic testing machine.

In accordance with these and other objects which will be apparent hereinafter, the present invention will be described with particular reference to the accompanying drawings.

PREFERRED EMBODIMENT OF THE INVENTION

Figure 1:
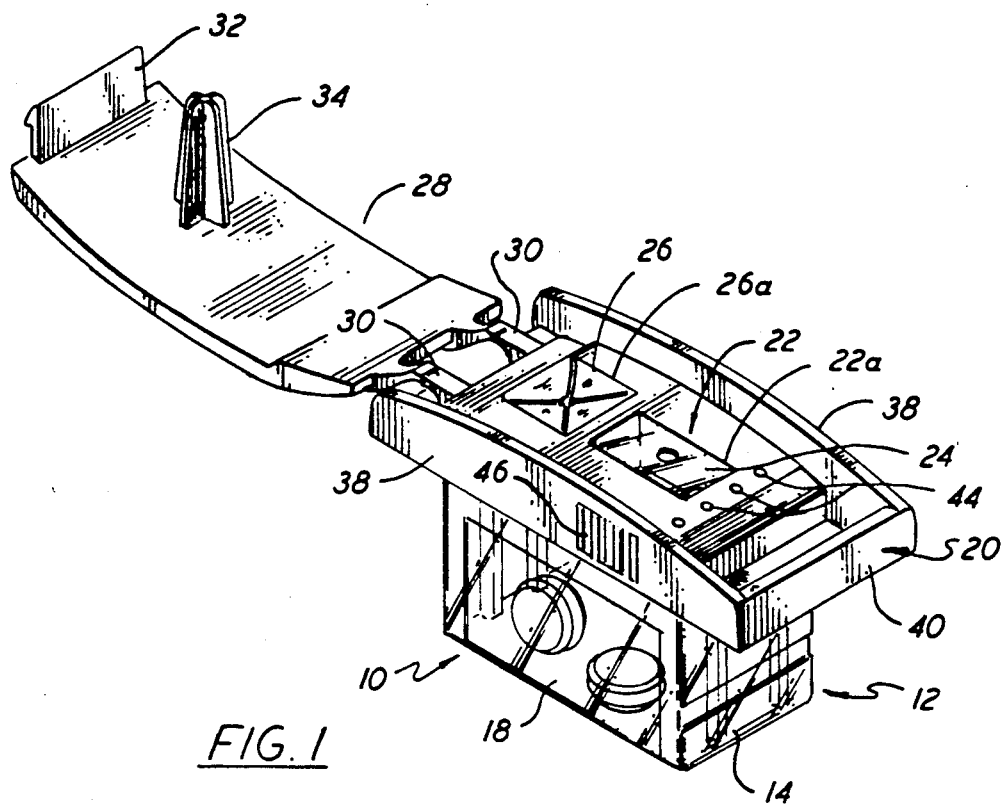
FIG. 1 is a perspective view of the present invention with the cap in the open position.

Referring now to the drawings, and in particular FIG. 1, the invention is shown generally at 10 comprised of transparent body 12 and a cover 20.

The cuvette body 12 is a vessel or hollow container that includes end walls 14 connected to side walls 18 and bottom wall 16 forming a hollow rectangular box with an open top. The body 12 may be molded as one piece from a clear acrylic material, which is impervious to moisture or atmosphere. The body material is selected to be sufficiently transparent to permit radiant energy absorption testing of a specimen or sample contained within the body which serves as a reaction chamber as will be further discussed. By way of example but not limitation, the dimensions of the cuvette body 12, stated in inches, may be 0.545 in length, 0.312 in width, and 0.545 in height. Of course the dimensions may vary widely without departing from the scope of the invention. It is important that the volume of the reaction chamber be such that the reaction chamber when filled acts to provide the exact volume for diluent added to the cuvette for a predetermined test.

The cuvette 10 also includes a cover 20 that is sonic welded or otherwise bonded to body 12. The cover 20 provides several elements that are important for the different operational testing stages in the automated machine.

Figure 2:
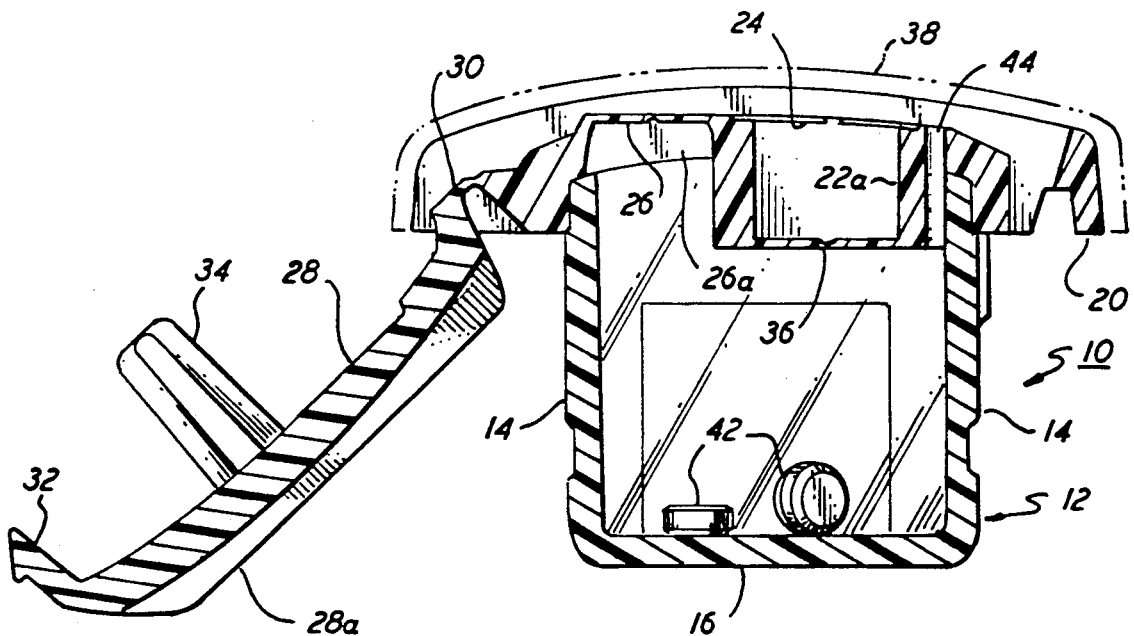
FIG. 2 is a side elevational view of the invention in cross section, with the cap in the open position.
Figure 3:
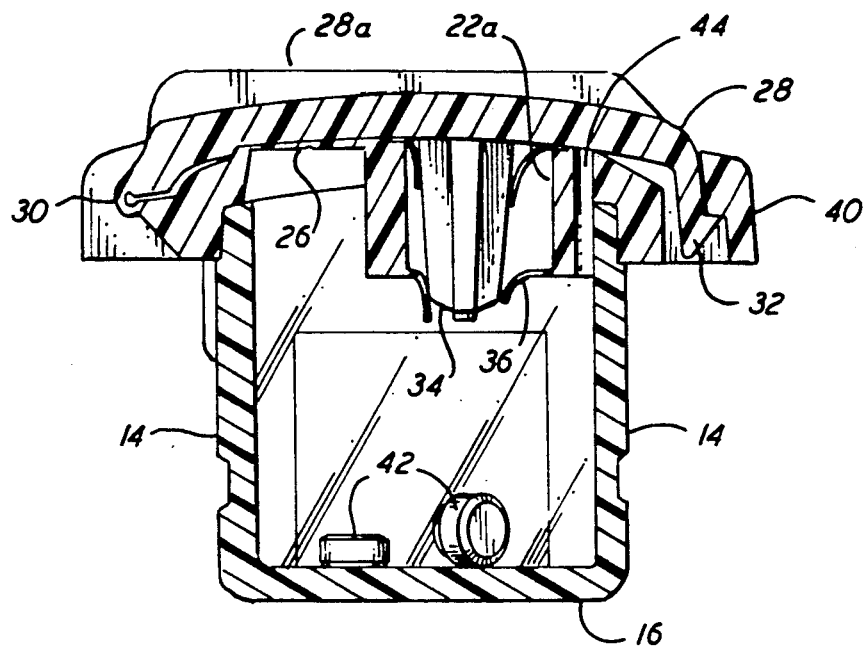
FIG. 3 is a side elevational view of the present invention, in cross section, with the cap in the closed position.
Figure 4:
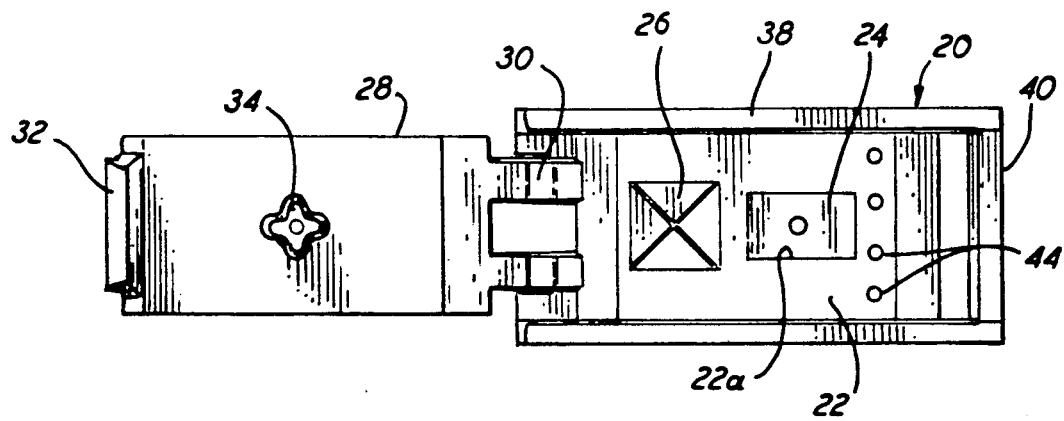
FIG. 4 is a top plan view of the invention with the cap in the open position.

As shown in FIGS. 2, 3, and 4, these elements include the sample or specimen receiving chamber formed by the cover barrier wall 22 having a vertical passage 22a sealed at its lower end by a frangible, thin floor 36 and partially covered at its upper end by a thin film 24 having a circular opening near its center for receiving the end of a pipette. The cover passage 22a in conjunction with the bottom floor 36 form the receiving chamber for serum or sample that is introduced by pipette through the opening in thin film 24.

Another important element of cover 20 is a second vertical passage 26a that is partially covered by flaps 26 at its upper end. The flaps 26 are flexible and may be opened downwardly by a pipette or other conduit shaped injector to permit the introduction of a diluent into the reaction chamber formed by body 12.

The cover 20 also has four 0.005 inch diameter vent holes 44 that are very important in the operation of the cuvette. The vent hole diameter is sized appropriately so that air is vented to the outside as the diluent flows into the reaction chamber. When the chamber is full, the surface tension created by the 0.005 inch diameter holes prevents any overflow of diluent through the vent holes 44.

The cover 20 includes a cap 28 attached by hinges 30. Protruding from one side of cap 28 and substantially perpendicular thereto is a lancet-like post 34 having a "cross" shaped cross section relative to its longitudinal axis. The post 34 is sized in length and positioned relative to hinges 30 such that when cap 28 is closed over cover 20, post 34 will be moved into passage 22a (serum receiving chamber) piercing an opening in floor 36. The floor 36 is connected to the chamber side walls 22a such that it cannot be detached by the action of post 34. (If detached, floor 36 might interfere with light passage through the cuvette.) Also attached to cap 28 is a latch 32.

After the serum or sample has been manually added to the receiving chamber 22a, the cuvette is now ready to be loaded into an automated testing machine. Note that the cap 28 is in the open position when the cuvette is placed in the test machine. Once in the machine, the cuvette bar code label is read and the test parameters are automatically set. Next the diluent is automatically dispensed into the cuvette and a vibrating mixing action takes place. After the reagent and diluent are fully mixed, a baseline radiant energy absorption reading is taken. After this initial measurement, an interposer with roller bearing mechanism (not shown) in the machine closes the cap 28, and the cuvette, now sealed, is vibrated. As the cap 28 is closed, the post 34 breaks through the sample chamber floor 36, allowing the sample to be mixed with the reagent-diluent mixture, aided by the vibration. With the cap in the closed position, the cuvette is completely sealed such that its contents cannot escape. The cap 28 is fastened by the engagement of latch 32 with a flange on bar 40. The machine can now complete the test on the sample.

The cover 20 may be made from high impact styrene and sonic welded to the upper rim of body 12. Hinges 30 and cap 28 may be formed with the cover 20, with hinges 30 being "living" hinges.

Figure 5:
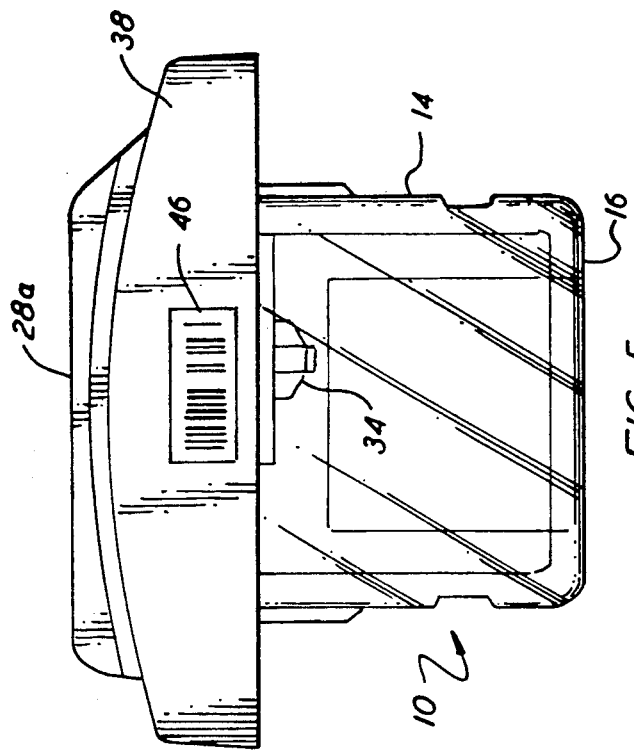
FIG. 5 is a side elevational view of the invention with the cap in the closed position.
Figure 6:
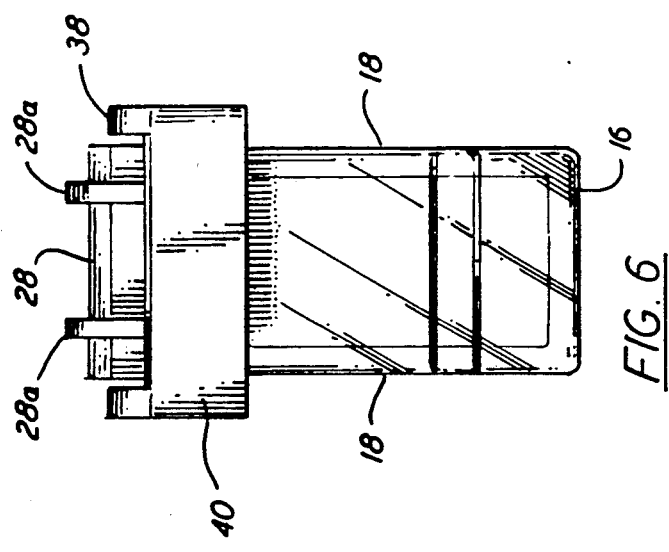
FIG. 6 is an end elevational view of the invention looking at the end farther from the cap hinge.

FIGS. 5 and 6 show the cuvette 10 after the cap 28 is closed. The cuvette, in accordance with the invention described herein, is designed for use in an automated testing machine. The cap 28 includes parallel ridges 28a that project above the upper surface of cap 28 to act as cap stiffeners and a bearing contact surface for mechanically closing the cap.

Figure 7:
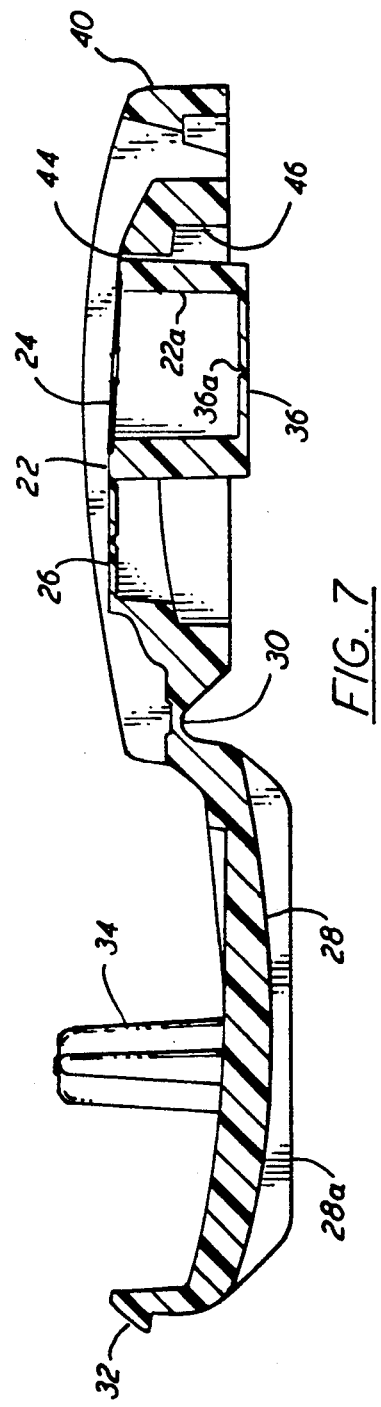
FIG. 7 is an enlarged side elevational view of the invention, in cross section, with the cap in the open position.

FIG. 7 shows the cover 20 and the serum or sample receiving chamber 22a and molded bottom floor 36 with a thinner flash section 36a (formed in an "X" shape) to provide break lines when the post 34 applies pressure as the cap 28 is closed.

The top of the serum chamber 22a is partially covered by hot stamped film 24. Film 24 has a small opening burned in the center to act as access for the end tip of a pipette containing serum or sample and also to wipe the pipette tip dry as it is removed from the chamber 22a.

The top surfaces of the diluent access are (flaps 26 and adjacent area) are made parallel to the underside surface of the cap 28 that abuts the diluent access perimeter in order to provide a parallel seat for the machine actuated, diluent dispenser tip and achieve a good seal when the cap 28 is closed.

FIGS. 1 and 7 show vent holes 44 that aid in the filling of the reagent chamber with diluent by allowing air that would otherwise be trapped in the reaction chamber to escape. Note that the diameter of each vent hole is sized so that diluent will not escape through the vent holes because of the surface tension of the diluent over the vent opening. However, the vent holes are sealed from the ambient air when the cap is closed. After the test has been completed, the cuvette can be safely discarded because the contents are sealed from the ambient surroundings.

The cuvette and the specific test to be performed therein (dependent upon the kind and quantity of reagent it contains) is identified by labels 46 adhesively attached to each side 38 of the cover. One label on one side would have a machine readable bar code while the other side label would display a letter or number code that is easily identified by the test operator.

Figure 8:
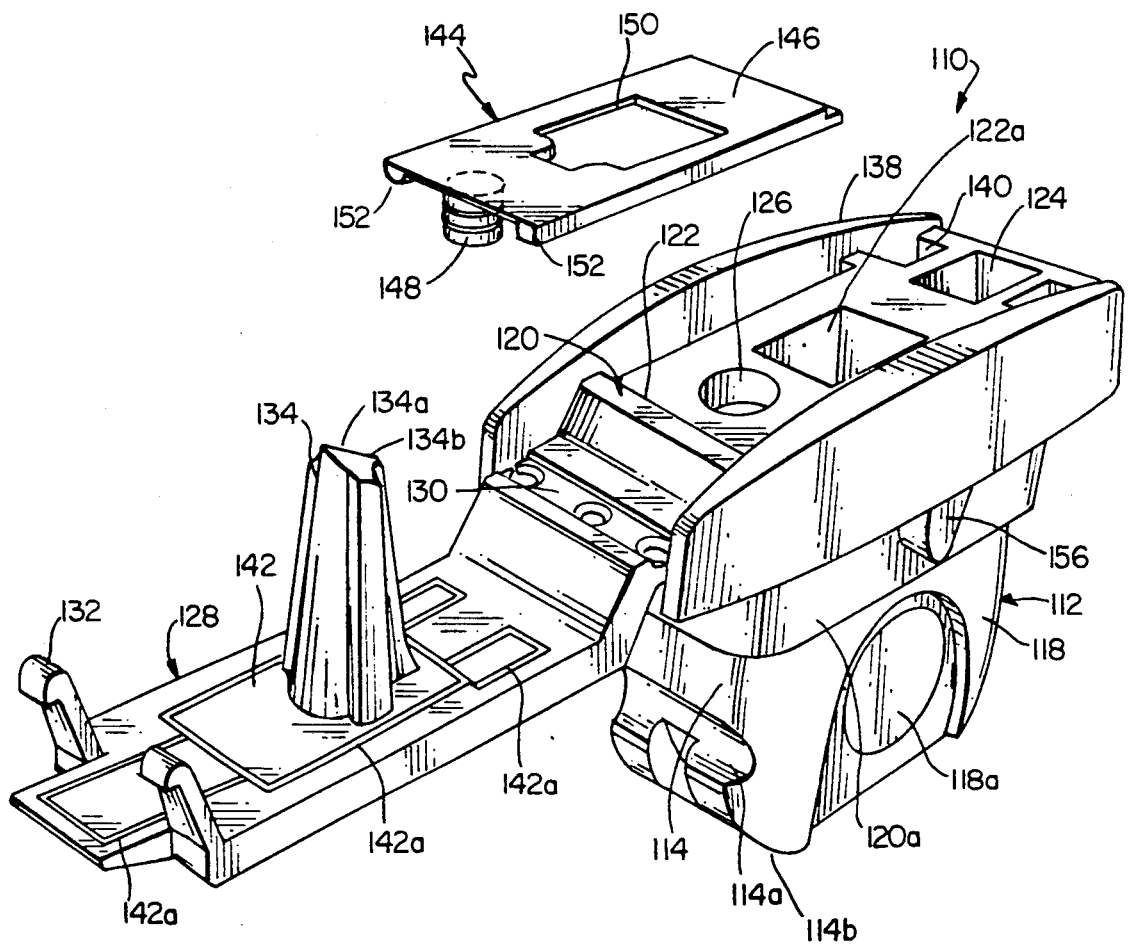
FIG. 8 is a top perspective view of an alternate embodiment of the invention that includes (as shown exploded) a gasket plug panel that is affixed to the top of the cover.

Referring now to FIG. 8 an alternate embodiment of the invention is shown which is used with a liquid reagent. The liquid reagent is prepackaged in the cuvette at the factory. By using a liquid reagent, it is not necessary to provide the liquid diluent required with a dry reagent in the automated test device when performing a test. Therefore, in general, the cuvette 110 is modified (1) by eliminating the vent holes which are required when using a dry reagent that requires diluent and (2) by adding an additional sealing panel 144 which will be described in greater detail below. The cuvette 110 is comprised of a hollow body 112 (providing a rectangular parallelepiped interior chamber) that includes side walls 118 uniformly molded as a single unit with end walls 114 and a bottom wall 116 (FIG. 9) forming a hollow receptacle for receiving a liquid reagent, prepackaged at the factory. The side walls 118 include an optically clear window 118a on opposite side walls 118 to permit the optical or ocular testing for the liquid reagent alone and when subsequently mixed with the specimen. One locating key 156 is centered on each side to locate the cuvette with respect to the automated testing machine.

The cover 120 is ultrasonically or otherwise bonded to the body 112 and includes a circular aperture 126 and a flat top wall 122 that includes a specimen chamber formed by side walls 122a and bottom trap doors 136 which are sealed together initially but are frangibly openable by action of post 134 when the cap 128 is closed in the automated test machine. A purge reservoir 124 for purging the diluent dispenser tip in the automated equipment is provided to wash out residual reagent and prevent carry over into the next or following cuvette which may contain a different reagent. The cover 120 includes a pair of arched side members 138 which function and interact with the automated machine as a roll down surface.

A sealing panel 144 is employed solely with a cuvette using a liquid reagent, eliminating the need for a diluent. The upper surface of top wall 122 also includes grooves 154 longitudinally disposed along each edge which receive glands 152 in the gasket/plug sealing panel 144 to firmly seal panel 144 over the cover surface 122. The panel 144 also includes an aperture 150 which permits access to the specimen chamber defined by walls 122a so that the specimen can be added to the specimen chamber.

The cap 128 includes a modified post 134 having inclined surfaces 134b terminating in knife-like edge end tip 134a which acts as a plunger for piercing the specimen chamber trap doors 136 at the centerline of the doors to ensure proper separation to effect direct hinge action of the doors 136 to release the specimen into the cuvette body 112 containing the liquid reagent.

Figure 9:
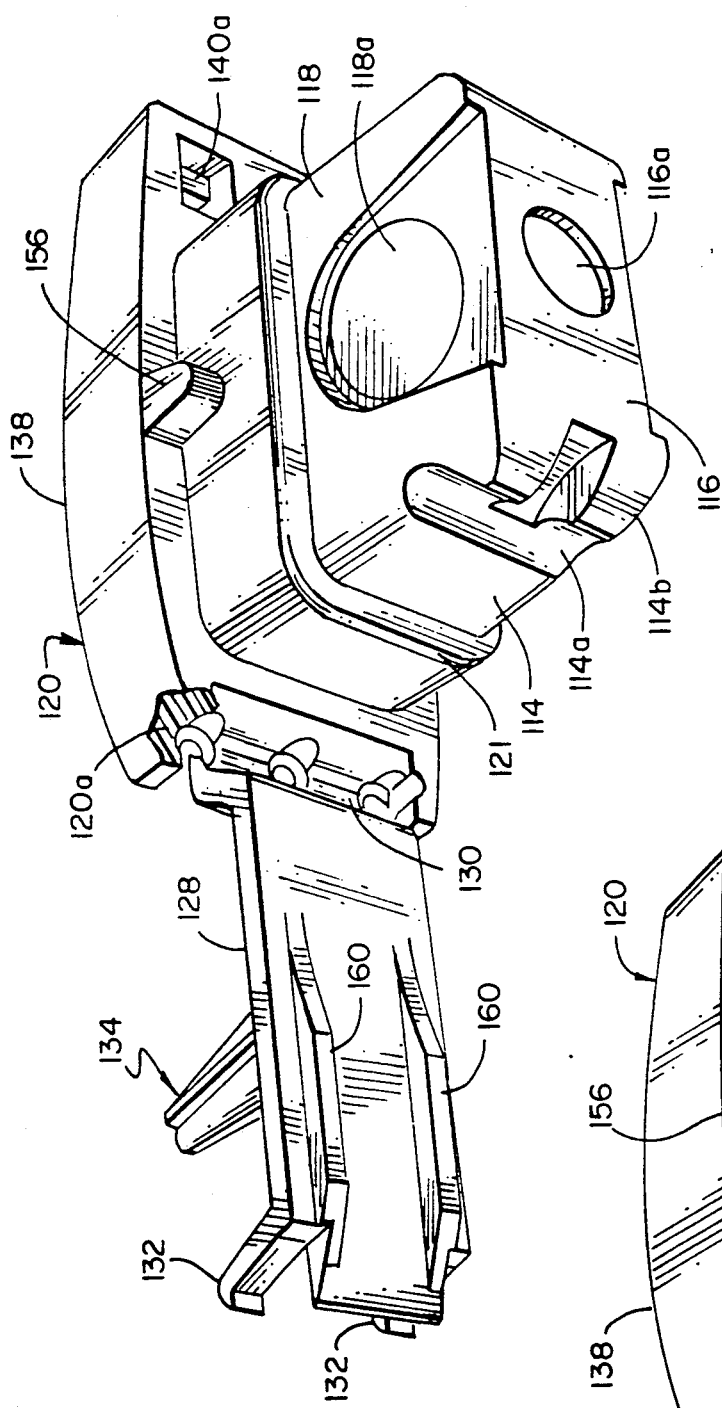
FIG. 9 shows a bottom perspective view of the alternate embodiment of the invention.

Referring now to FIG. 9 the cuvette 110 is shown from a bottom perspective view disclosing the bottom wall 116 having an optically clear window 116a which permits fluorescent polarization and nephlometric type tests.

The cap 128 is unitarily connected by a hinge 130 which also acts to seal the end of the cuvette when the cap 128 is closed over the cover 120.

The cap 128 includes a pair of parallel ridges 160 which interact with the automated machine and rollers for closing the cap 128 and resulting in a secure latching of the cap.

A pair of snaps 132 which are integrally formed with the cap 128 are engaged into slot edges 140a at the opposite end of cover 120 to firmly attach the cap to cover the which the cap is closed resulting in a leak-proof seal.

Referring back to FIG. 8, in the manufacture of the liquid reagent model, the plug/gasket sealing panel 144 is firmly attached at the factory to the top of cuvette cover 120 after the liquid reagent has been inserted into the cuvette body 112 chamber. With the panel 144 attached, the liquid reagent is sealed tightly within the cuvette by action of the panel 144 which includes plug 148 received into aperture 126 and the fact that the specimen trap doors 136 in the specimen chamber 122a are also sealed.

To perform a test using the liquid reagent model, the specimen is added to the specimen chamber 122a at the testing site, which may be a doctor's office, laboratory or the like. The cuvette 110 then is inserted into the automatic testing machine in the cuvette's cap open position as shown in FIG. 8. The automated machine can first test the liquid reagent alone in its present state (before the specimen is mixed) while the cuvette 110 is located at a test station in the automatic testing machine. After a first measurement of the liquid reagent is obtained, optically or ocularly, then the testing machine closes the cap 128, causing the post 134 to fracture and open the two inclined trap doors 136 causing the specimen to be received into the interior chamber of cuvette body 112 containing the liquid reagent. The cuvette is then boosted for mixing, causing a rocking action on its radius corners adjacent the bottom floor 16, greatly increasing the mix action. A second measurement is then obtained optically or ocularly of the liquid reagent-specimen mixture and the results calculated by the testing machine.

A raised sealing bead 142a (FIG. 8) is disposed about the surface of cap surface 142. The bead is a raised portion such that when cap 128 is closed firmly against panel 144 (made of a silicone rubber), the bead 142a will be impressed into the silicone rubber of panel 144, forming a tight liquid impervious and air impervious seal about the cover top surface 122 including the purge chamber 124.

Figure 10:
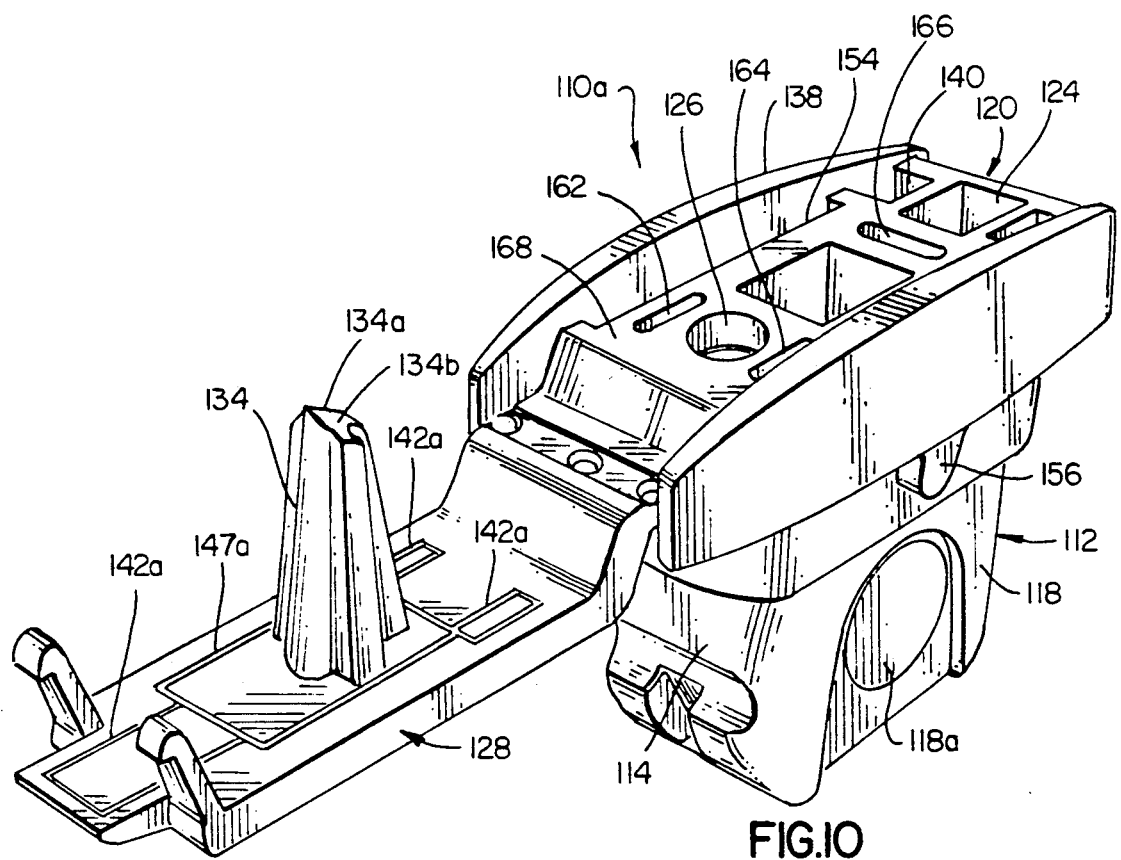
FIG. 10 shows yet another embodiment of the invention that is used with a prepackaged dry reagent only.

Referring now to FIG. 10, a modified cuvette 110a for use with a prepackaged dry reagent (powdered or capsule) is shown which is inserted in the cuvette body 112. Note that in this embodiment the plug/gasket panel 144 (FIG. 8) is not used. The aperture 126 acts to receive a diluent dispensing probe in the automated machine (not shown) for dispensing diluent into the cuvette body 112 that houses the dry reagent. The diluent is added at the test site while performing the test in the automated machine. The purge reservoir 124 collects diluent purged from the diluent dispensing tip (not shown) after the dispensing tip has been withdrawn from aperture 126 during the testing process. In this alternate embodiment three vent slots 162, 164 and 166 are provided which collectively allow for air to escape from the cuvette body 112 while the diluent is being added.

A thin frangible film 168 of hydrophobic metricel polypropylene is used to cover the vent holes 162, 164 and 166 and diluent aperture 126, specimen chamber 122a and the purge reservoir 124. The film 168 in gas permeable which allows air to vent through the vent slots during diluent dispensing while also allowing easy fracture for insertion of the specimen into the specimen chamber 122a. The film 168 provides another benefit in that the sealing beads 142a in cap 128 will also engage the thin film when the cap 128 is closed and locked over cover 120 again ensuring that the cuvette is sealed after the test is completed. The film is attached to the cover surface by a suitable glue.

Figure 11:
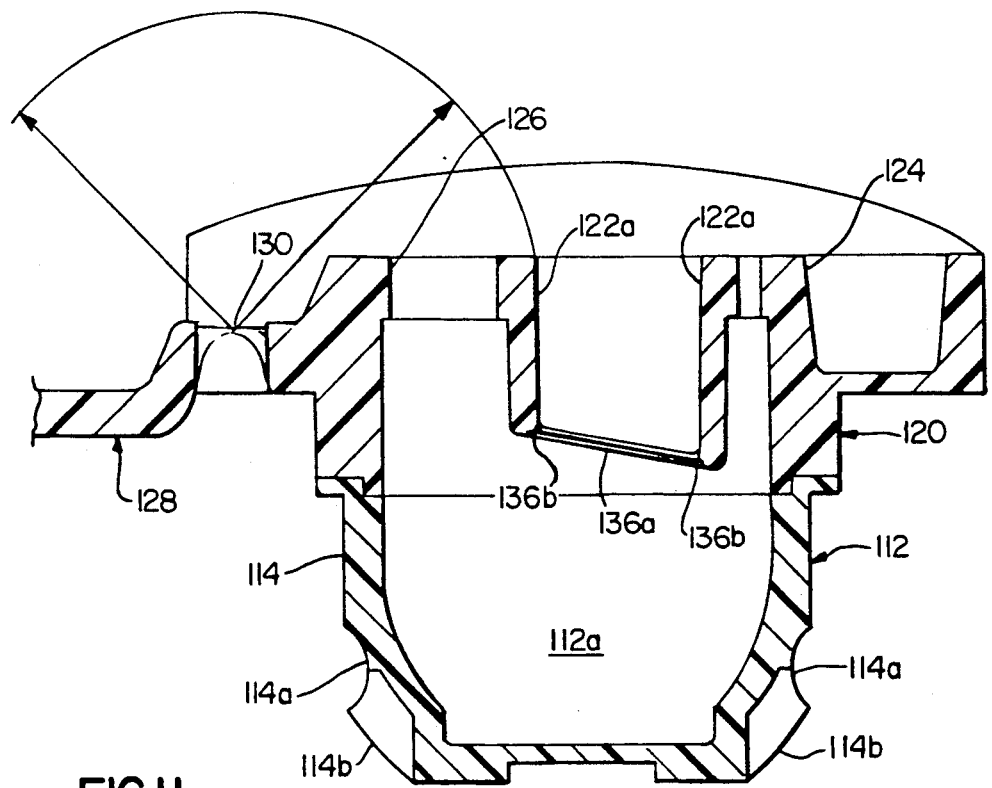
FIG. 11 shows a side elevational cross sectional view of the alternate embodiment construction of the cuvette body and the specimen receiving chamber.

In this embodiment the cuvette 110a functions similarly to the original cuvette 10 discussed in FIGS. 1 through 7 with regard to the powdered and capsule reagents in term of operation and the automat FIGS. 9 and 11 show another improvement in the alternate embodiment of the invention that functions with a carousel in the automated test machine which carries each cuvette through the automated test machine. As shown in FIGS. 9 and 11, the side end wall 114 includes, on each end, a lateral, concave channel 114a which acts to receive snap legs which are in the automated test machine (not shown) to firmly hold the cuvette in position relative to the carousel and the machine. Also the lower corners 114b formed by the side walls 114 and the bottom wall 116 have equal predetermined radii of curvatures. At a particular stage in the automated test machine, the curved corners 114b engage surfaces having comparable curvatures on the snap legs to produce a rocking motion whenever the carousel is moved backward and forward to induce vigorous mixing within the cuvette after the specimen has been introduced to the reaction chamber and the cap is closed. Thus the curved end portions 114b while engaging a similar surface of curvature on the snap legs will permit a rocking motion back and forth for improved mixing action. The bottom wall surface 116 is substantially flat to permit a roller or wheel in the automated test machine to raise the cuvette, disengaging the snap legs from the snap leg detent 114a at the mixing stage in the machine. Thus the cuvette is configured on its outside and bottom walls to allow the snap legs in the automated testing machine to accomplish the dual purposes of allowing for rocking the cuvette for mixing while in the other stages to secure the cuvette in position in the carousel.

Figure 12:
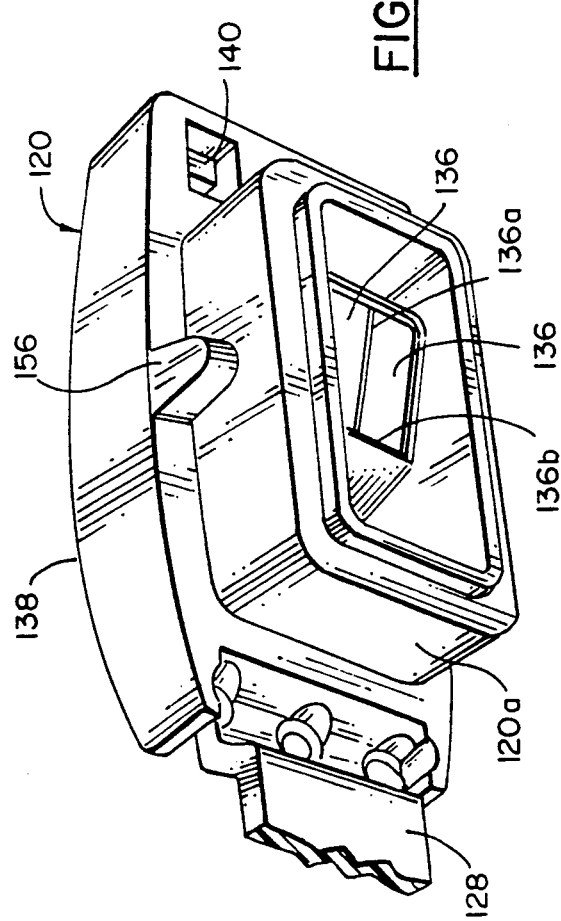
FIG. 12 shows a bottom perspective view of the cover used in the alternate embodiment of the invention.

FIGS. 11 and 12 show the specimen receiving chamber defined by walls 122a and bottom trap doors 136 which are sealed together along a frangible center line 136a forming the bottom of the specimen chamber 122a.

The bottom trap doors 136 are inclined to reduce possible trapping of bubbles when diluent or liquid reagent are dispensed through aperture 126. In their initial state the hinged doors 136 are joined together and to the walls 122a of the specimen chamber so that the compartment is sealed from the body 112 chamber. The post 134 size and shape is configured to more easily fracture and open the trap doors 136 in the specimen chamber when the cap 128 is closed tightly over the cover of the cuvette. In the cross section as shown, the linear weakened portions 136a and 136b between the walls 122a and the doors 136 form an "H" shape. The trap doors 136 remain sealed until forced open by the post 134 which causes the centerline 136a and the wall edges 136b to frangibly detach forcing the doors to open much like a pair of trap doors. Note that the bottom floor is inclined relative to the horizontal which aids in dispensing the specimen into the reagent containing chamber 112. Note also from FIGS. 8 and 10 that the post 134 end tip includes a pair of inclined surfaces 134b terminating in the edge 134a which meets the centerline 136a of the trap doors 136 when the cap is closed aiding the doors 136 to spread open from the center position. This allows the specimen to completely received into the mixing chamber 112a where it mixes with either the dry reagent and diluent mixture or with a liquid reagent.

FIGS. 11 and 12 also show hinge 130 that connects the cap 128 (partially shown) unitarily to the cover 120.

The present invention provides a disposable, non-reuseable cuvette that allows a technician in a doctor's office or laboratory to perform a variety of medical diagnostic tests quickly, safely, accurately and inexpensively by significantly reducing the technician loading activities required and the structural complexity of the cuvette and its interaction with the testing machine.

The instant invention has been shown and described herein in what it is considered to be the most practical and preferred embodiment. It is recognized however that departures may be made therefrom within the scope of the invention and that obvious modifications will occur to a person skilled in the art.

What I claim is:

1. A cuvette for performing an automatic diagnostic test on a specimen comprising:
   a hollow body having a bottom wall and a plurality of side walls unitarily formed defining a rectangular reagent receiving chamber, at least two opposing side walls having windows sufficiently transparent to permit radiant energy transmission for optical or ocular testing;
   a substantially rectangular cover having a flat central portion and raised sides ridges, said cover sealed to the upper end of said hollow body side walls, said cover including a specimen chamber having side walls extending downwardly from a specimen chamber aperture in said cover, said specimen chamber including a pair of movable closures forming the bottom floor of said specimen chamber, said movable closures initially joined together along opposing edges and including a frangible joint therebetween, each removable closure hingedly connected to said opposite specimen chamber side walls, said cover including an aperture for receiving a liquid dispensing probe for dispensing a liquid into said reagent receiving chamber;
   a sealing cap having an upper surface and a lower surface relative to closed position for sealing said cover openings, said sealing cap hingeably connected to one end of said cover, said cap including an elongated post extending substantially perpendicularly from the lower surface of said cap and positioned and sized to engage and open the movable closures forming the bottom wall in said specimen chamber whenever said cap is in a closed position over said cover;
   said specimen chamber for floor including said movable closures is inclined angularly relative to the bottom wall of said hollow body to reduce the possible trapping of bubbles when diluent or liquid reagent are being dispensed into said reagent chamber.

2. A cuvette as in claim 1, including:
   a raised bead disposed in predetermined areas around the periphery of the cap lower surface to aid in sealing the cap to said cover when said cover is in a closed position.

3. A cuvette as in claim 1, wherein:
   said cap post is configured to include an elongated shaft body and a shaft tip, said shaft body having a cross-shaped cross section and said shaft tip having a pair of flat surfaces angularly inclined relative to each other to form a knife-like edge substantially aligned with the centerline between said movable closures of said specimen chamber when said cap is closed.

4. A cuvette as in claim 1, wherein:
   a purge reservoir formed in said cover near one end of said cover, said purge reservoir including a plurality of walls and a floor formed within the cover structure.

5. A cuvette for use with a liquid reagent as in claim 4, including:
   a sealing gasket sized to fit over a predetermined portion of said upper cover surface, said sealing gasket including a plug that is received into said diluent receiving aperture, and a specimen chamber aperture to permit access to said specimen chamber.

6. A cuvette for use with a dry reagent as in claim 4, including:
   air venting means provided through said cover surface layer to vent said reagent chamber; and
   thin gas permeable film affixed to said flat central cover portion, overlaying said dispensing probe aperture, said specimen chamber aperture and said venting means.

7. A cuvette as in claim 4, wherein:
   said hollow body bottom wall includes a window sufficiently transparent to permit transmission of radiant energy for fluorescent polarization and nephlometric testing.

8. A cuvette as in claim 4, wherein:
said hollow body side walls and bottom wall having exterior surfaces including detents strategically located for engagement with snap legs in said automated test machine and forming edges of a predetermined radius of curvature to permit vigorous rocking motion of said cuvette in said automated test machine.

* * * * *